United States Patent [19]

Nanthavong et al.

[11] 4,115,401
[45] Sep. 19, 1978

[54] PROSTAGLANDIN DERIVATIVES AND PROCESS FOR PREPARING THE SAME

[75] Inventors: Souli Nanthavong, Grenoble; Charles Pigerol, Saint-Quen; Pierre Eymard, Fontaine; Jacques Simiand, Noyarey, all of France

[73] Assignee: Labaz, Paris, France

[21] Appl. No.: 783,284

[22] Filed: Mar. 31, 1977

[30] Foreign Application Priority Data

Mar. 31, 1976 [IL] Israel ........................................ 49325

[51] Int. Cl.² .......................................... C07D 207/12
[52] U.S. Cl. ............................... 260/326.43; 260/961; 424/274
[58] Field of Search ................... 260/326.43; 424/274

[56] References Cited

U.S. PATENT DOCUMENTS 3,975,399  8/1976  DeFranco et al. ................ 260/326.2

OTHER PUBLICATIONS

Robert Morrison and Neilson Boyd, "Organic Chemistry," 3rd ed., Allyn and Bacon, Inc., Boston, (1974).

Primary Examiner—Donald G. Daus
Assistant Examiner—Lisa Jones
Attorney, Agent, or Firm—Mason, Kolehmainen, Rathburn & Wyss

[57] ABSTRACT

Prostaglandin derivatives corresponding to the general formula:

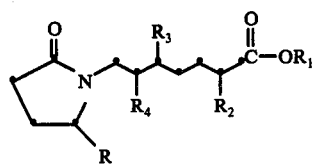

wherein $R_1$ represents hydrogen, methyl or ethyl, $R_2$, $R_3$ and $R_4$, which are the same or different, each represent hydrogen or methyl and R is selected from the groups consisting of:

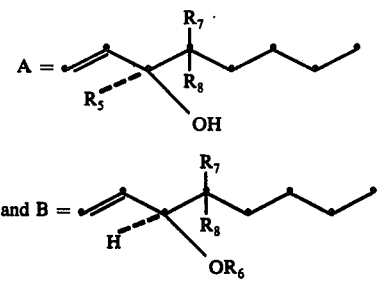

in which $R_5$ represents hydrogen, methyl or ethyl, $R_6$ represents methyl, ethyl or acetyl and $R_7$ and $R_8$, when they are different, each represent hydrogen or a branched- or straight-chain alkyl group having from 1 to 7 carbon atoms or $R_7$ and $R_8$, when they are identical, each represent hydrogen or a straight-chain alkyl group having from 1 to 3 carbon atoms with the provisos that:
when both $R_7$ and $R_8$ represent hydrogen, $R_5$ is methyl or ethyl,
when $R_5$ represents methyl and $R_2$, $R_3$, $R_4$, $R_7$ and $R_8$ all represent hydrogen then $R_1$ is ethyl,
the said prostaglandin derivatives being in the form of a mixture of isomers or of an individual isomer. They are useful in the treatment of pathological states which affect the respiratory system.

14 Claims, No Drawings

PROSTAGLANDIN DERIVATIVES AND PROCESS FOR PREPARING THE SAME

This invention relates to the prostaglandins and is concerned with novel compounds related in structure to prostaglandin $E_1$ which has the structural formula:

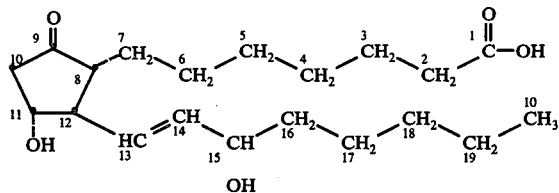

and to a process for preparing the said novel compounds.

Prostaglandin $E_1$ is normally abbreviated to "$PGE_1$". In accordance with common usage the formula of $PGE_1$ can also be written as:

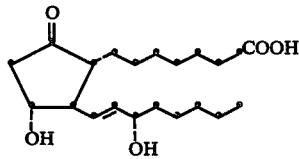

The compounds with which the present invention is concerned are those corresponding to the general formula:

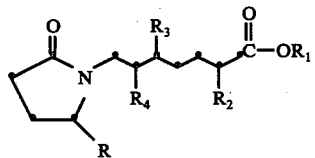

wherein $R_1$ represents hydrogen, methyl or ethyl, $R_2$, $R_3$ and $R_4$, which are the same or different, each represent hydrogen or methyl and R is selected from the groups consisting of:

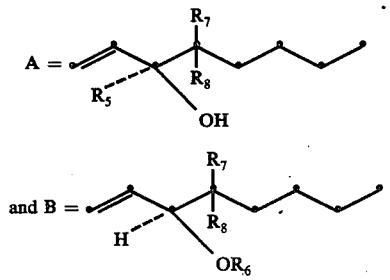

in which $R_5$ represents hydrogen, methyl or ethyl, $R_6$ represents methyl, ethyl or acetyl and $R_7$ and $R_8$, when they are different, each represent hydrogen or a branched- or straight-chain alkyl group having from 1 to 7 carbon atoms or $R_7$ and $R_8$, when they are identical, each represent hydrogen or a straight-chain alkyl group having from 1 to 3 carbon atoms with the provisos that: when both $R_7$ and $R_8$ represent hydrogen, $R_5$ is methyl or ethyl, when $R_5$ represents methyl and $R_2$, $R_3$, $R_4$, $R_7$ and $R_8$ all represent hydrogen then $R_1$ is ethyl.

One class of compounds falling within the definition of formula I consists of the prostaglandin derivatives represented by the said formula I wherein $R_1$ represents hydrogen, methyl or ethyl, $R_2$, $R_3$ and $R_4$ each represent hydrogen or methyl and R is selected from the groups A and B wherein $R_5$ represents hydrogen, methyl or ethyl, $R_6$ represents methyl, ethyl or acetyl and $R_7$ and $R_8$, when they are different, each represent hydrogen or a branched-or straight-chain alkyl group having from 1 to 7 carbon atoms or $R_7$ and $R_8$, when they are identical, each represent hydrogen or a straight- chain alkyl group having from 1 to 3 carbon atoms with the proviso that at least one of the groups $R_2$, $R_3$ and $R_4$ is methyl.

A pharmacologically preferred class of compounds with which the invention is concerned consists of the prostaglandin derivatives of formula I wherein $R_1$ represents hydrogen, methyl or ethyl, $R_2$, $R_3$ and $R_4$ each represent hydrogen or methyl and R is selected from the groups A and B wherein $R_5$ represents hydrogen, methyl or ethyl, $R_6$ represents methyl or acetyl and $R_7$ and $R_8$, which are identical, each represent hydrogen or methyl with the provisos that:

when both $R_7$ and $R_8$ represent hydrogen, $R_5$ is methyl or ethyl, when $R_5$ represents methyl and $R_2$, $R_3$, $R_4$, $R_7$ and $R_8$ all represent hydrogen, then $R_1$ is ethyl, when $R_6$ represents methyl and $R_2$, $R_3$, $R_4$, $R_7$ and $R_8$ all represent hydrogen, then $R_1$ is methyl.

Examples of compounds of this class are:

DL-Φ-carboethoxy-1-hexyl-5-(3'-hydroxy-3'-methyl-1'-octen-(E)-yl)-2-pyrrolidinone or DL-8-aza-11-deoxy-15 methyl-$PGE_1$ ethyl ester.

DL-ω-carboethoxy-1-hexyl-5-(3'-hydroxy-3'-ethyl-1'-octen-(E)-yl)-2-pyrrolidinone or DL-8-aza-11-deoxy-15-ethyl-$PGE_1$ ethyl ester.

DL-ω-carboxy-1-hexyl-5-(3'-hydroxy-3'-ethyl-1'-octen-(E)-yl)-2-pyrrolidinone or DL-8-aza-11-deoxy-15-ethyl-$PGE_1$.

DL-ω-carboethoxy-1-hexyl-5-(3'-acetoxy-1'-octen(E)-yl)-2-pyrrolidinone or DL-8-aza-11-deoxy-15-0-acetyl-$PGE_1$ ethyl ester.

DL-ω-carboxy-1-hexyl-5-(3'-acetoxy-1'-octen-(E)-yl)-2-pyrrolidinone or DL-8-aza-11-deoxy-15-0-acetyl-$PGE_1$.

DL-ω-carbomethoxy-1-hexyl-5-(3'-methoxy-1'-octen-(E)-yl)-2-pyrrolidinone or DL-8-aza-11-deoxy-15-0-methyl-$PGE_1$ methyl ester.

DL-ω-carboethoxy-1-hexyl-5-(4',4'-dimethyl-3'-hydroxy-1'-octen-(E)-yl)-2-pyrrolidinone or DL-8-aza-11-deoxy-16,16-dimethyl-$PGE_1$ ethyl ester.

DL-ω-carboxy-1-hexyl-5-(4',4'-dimethyl-3'-hydroxy-1'-octen-(E)-yl)-2-pyrrolidinone or DL8-aza-11-deoxy-16,16-dimethyl-$PGE_1$.

DL-1-(6'-carboethoxy-6'-methyl-hexyl)-5-(3'-hydroxy-1'-octen-(E)-yl)-2-pyrrolidinone or DL-2-methyl-8-aza-11-deoxy-$PGE_1$ ethyl ester.

DL-1-(6'-carboxy-6'-methyl-hexyl)-5-(3'-hydroxy-1'-octen-(E)-yl)-2-pyrrolidinone or DL-2-methyl-8-aza-11-deoxy-$PGE_1$.

DL-1-(6'-carboethoxy-2'-methyl-hexyl)-5-(3'-hydroxy-1'-octen-(E)-yl)-2-pyrrolidinone or DL-6-methyl-8-aza-11-deoxy-$PGE_1$ ethyl ester.

DL-1-(6'-carboxy-2'-methyl-hexyl)-5-(3'-hydroxy-1'-octen-(E)-yl)-2-pyrrolidinone or DL-6-methyl-8-aza-11-deoxy-$PGE_1$.

DL-1-(6'-carboethoxy-3'-methyl-hexyl)-5-(3'-hydroxy-1'-octen-(E)-yl)-2-pyrrolidinone or DL-5-methyl-8-aza-11-deoxy-PGE$_1$ ethyl ester.

DL-1-(6'-carboxyl-3'-methyl-hexyl)-5-(3'-hydroxy-1'-octen-(E)-yl)-2-pyrrolidinone or DL-5-methyl-8-aza-11-deoxy-PGE$_1$.

The compounds of formula I possess isomeric centres and thus can be produced as optical isomers, position isomers or mixtures of these isomers. The mixtures of these isomers can be resolved, if desired, at appropriate stages by methods known to those skilled in the art to obtain the respective individual isomers.

It is to be understood that these isomers as well as mixtures thereof are included within the scope of the present invention.

The compounds of formula I wherein R$_1$ represents hydrogen, R$_2$, R$_3$ and R$_4$ have the meaning cited therein and R represents the group A or the group B wherein R$_6$ represents methyl or ethyl can be prepared by saponification in an alcoholic medium such as methanol, of an ester corresponding to the general formula:

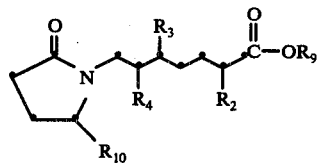

II wherein R$_2$, R$_3$ and R$_4$ have the same meaning as in formula I, R$_9$ represents a branched- or straight-chain alkyl group having from 1 to 7 carbon atoms and R$_{10}$ is selected from the groups consisting of the group A in formula I and the group:

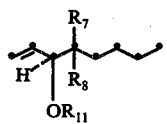

in which R$_7$ and R$_8$ have the same meaning as in formula I and R$_{11}$ represents methyl or ethyl, the saponification being effected by means of an alkali, for example sodium hydroxide, followed by hydrolysis of the resulting alkali metal salt of the compound of formula II by means of a strong acid, for example hydrochloric acid, to form the required compound of formula I.

The compound of formula I wherein R$_1$ represents hydrogen, R$_2$, R$_3$ and R$_4$ have the meaning cited therein and R represents the group B wherein R$_6$ represents acetyl, can be obtained by refluxing an acid of the general formula:

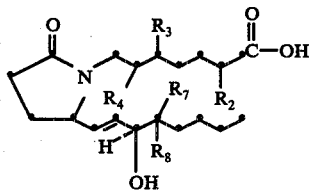

III in which R$_2$, R$_3$, R$_4$, R$_7$ and R$_8$ have the same meaning as in formula I with aqueous acetic acid, which provides the required compound of formula I.

The esters of formula I can be obtained by various methods according to their chemical structure. Thus, in accordance with the present invention, the esters of formula I wherein R$_2$, R$_3$ and R$_4$ have the meaning cited therein, R$_1$ represents methyl or ethyl and R represents the group A in which R$_5$, R$_7$ and R$_8$ have the meaning given, can be obtained from a pyrrolidinone derivative of the general formula:

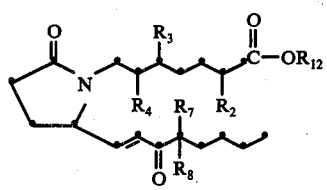

IV wherein R$_2$, R$_3$, R$_4$, R$_7$ and R$_8$ have the same meaning as in formula I an R$_{12}$ represents methyl or ethyl:

(a) When R$_5$ represents hydrogen by reduction with a suitable reducing agent, for example sodium borohydride in a inert medium, for example dimethoxyethane. The reduction in question can be carried out at a temperature between 0° and +5° C and preferably at 0° C.

(b) When R$_5$ represents methyl or ethyl, be treatment in an anhydrous ether, such as, for example, ethyl ether or tetrahydrofuran, with the bromide or iodide of methyl or ethyl magnesium, and subsequent hydrolysis of the resulting complex with, for example, a saturated aqueous solution of ammonium chloride to obtain the required ester of formula I. The treatment of the ketone in question of formula IV will be effected at a temperature between −15° C and 0° C, to obtain the required ester of formula I wherein R$_5$ represents methyl and at a temperature between −15° C and −5° C, preferably at −5° C, to obtain the required ester of formula I wherein R$_5$ represents ethyl. The esters of fromula I wherein R$_2$, R$_3$ and R$_4$ have the meaning cited therein, R$_1$ represents methyl or ethyl and R represents the group B, in which R$_7$ and R$_8$ have the meaning given, can be prepared as follows:

(c) When R$_6$ represents methyl or ethyl, be reacting at room-temperature and in an anhydrous ether, such as, for example anhydrous ethyl ether an acid of the general formula III hereabove, with methyl or ethyl iodide in the presence of an alkali metal hydride such as, for example, sodium hydride to obtain the ester of formula I wherein R$_1$ and R$_6$ are identical which, if desired, can be saponified by means of an alkali metal hydroxide, for example sodium hydroxide to obtain the corresponding acid which is then re-esterified with ethanol or methanol in an acid medium, for example sulphuric acid, to obtain the required ester wherein R$_1$ and R$_6$ are different.

(d) When R$_6$ represents acetyl, by reacting, in an appropriate solvent, such as, for example pyridine or methylene chloride and at room-temperature, an ester of the general formula:

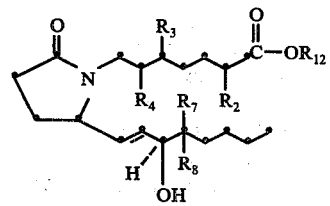

V wherein $R_2$, $R_3$, $R_4$, $R_7$ and $R_8$ have the same meaning as in formula I and $R_{12}$ represents methyl or ethyl, with acetyl chloride or acetic anhydride which provides the required ester of formula I.

As an alternative procedure, the esters of formula I, wherein R represents the group A in which $R_7$ and $R_8$ represent the substituents recited above and $R_5$ represents hydrogen, can be obtained by esterifying in an inert medium such as, for example methylene chloride and at room-tempreature an acid of the general formula III with either diazomethane of diazoethane which provides the required methyl or ethyl ester.

Among the starting-compounds represented by formula II those in which $R_9$ represents methyl or ethyl are also compounds included within the scope of formula I for which a process of preparation is described hereabove. The other esters of formula II can all be prepared in accordance with the aforesaid method given for the preparation of the methyl and ethyl esters of both formulae I and II.

The starting-compounds corresponding to formulae III and V are products included within the scope of formula I for which a process of preparation is described hereabove. With regard to the compounds of formula IV, these can be prepared by submitting a 5-carboxaldehyde-2-pyrrolidinone derivative of the formula:

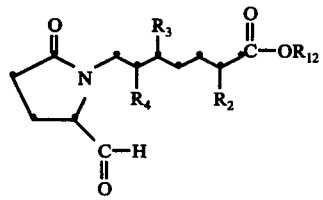
VI wherein $R_2$, $R_3$ and $R_4$ have the same meaning as in formula I and $R_{12}$ has the same meaning as in formula IV, to a Wittig reaction with a dimethyl 2-oxo-n-heptylphosphonate derivative of the formula:

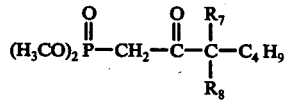
VII wherein $R_7$ and $R_8$ have the same meaning as in formula I so as to obtain the corresponding ketone.

The compunds of formula VI wherein $R_2$, $R_3$ and $R_4$ each represent hydrogen are known compunds having been described together with their process of preparation in French Pat. No. 2,304,340. The other compounds of formula VI can be prepared in accordance with the method set out in the said French Patent.

As regards the phosphorus-containing compunds of formula VII, these can be obtained by first reacting an appropriate ethyl hexanoate derivative with dimethyl methylphosphonate in the presence of butyllithium. The ethyl hexanoate derivatives in question are either known compounds or can be prepared in accordance with known procedures.

The compounds of the invention have been found to possess valuable pharmacological properties. Most of these properties are characteristic of the natural prostaglandins in general and of the prostaglandin $E_1$, also known as $PGE_1$, in particular. For example, the prostaglandin derivatives of the invention have shown that they exert a contracting action on the smooth intestinal and uterine muscles, a hypotensive and a vasodilatory effect as well as an inhibiting action on gastric secretion and on platelet aggregation. It has also been found that the prostaglandin derivatives of the invention have, in addition to their other properties, a bronchodilatory activity capable of being used particularly in the treatment of asthma and pathological states affecting the respiratory system.

Consequently, another object of the invention is to provide a method of treating, in a human or animal organism in need of such treatment, the various affections which are favourably influenced by the action of $PGE_1$ and, in particular, asthma or pathological states affecting the respiratory system, which method comprises administering to said organism an effective amount of at least one compound of formula I in the form of a mixture of isomers or of an active isomer, advantageously presented as a pharmaceutical or veterinary composition.

A further object of the invention is, therefore, a pharmaceutical or veterinary composition containing as essential active ingredient at least one compound of formula I in the form of a mixture of isomers or of an active isomer in association with a non-toxic carrier or excipient therefor.

Likewise, the invention also encompasses a method for preparing pharmaceutical and veterinary compositions whereby at least one compound of formula I in the form of a mixture or isomers or of an active isomer is associated with a non-toxic carrier or excipient therefor.

For several years, the prostaglandins have aroused particular interest at pharmacological and therapeutic levels. They are, in fact, natural compounds which are very widely distributed in the tissues of mammals and of which several have been isolated from human seminal liquids.

The prostaglandins have a very wide range of activity, which seems to result from their influence on the synthesis of 3', 5'-cyclic adenosine monophosphate (cyclic AMP).

According to their chemical configuration, they have various pharmacological actions such as hypertensive, hypotensive or anti-ulcerogenic activity or, depending on the part of the body concerned, a stimulating or relaxing effect upon smooth muscle, all of which actions become apparent a very closely related doses.

This lack of specificity on the part of natural prostaglandins is moreover responsible for most of the secondary effects which they can produce.

Of the natural prostaglandins, the prostaglandin referred to above and known as $PGE_1$ seems to be amongst the most active, as has been shown in Chimie Therapeutique 1, 34 (1969). $PGE_1$ is for example capable of stimulating the intestinal and uterine smooth muscle, of causing vasodilation and bronchodilation, of reducing gastric secretion and inhibiting platelet aggregation at infinitesimal doses of the order of a nanogram.

However $PGE_1$ has certain disadvantages which are inherent in the natural prostaglandins, because of its lack of specificity. For example, $PGE_1$, by its spasmogenic action on the alimentary canal will produce certain side-effects such as nausea, vomiting and diarrhoea.

It is therefore desirable to have available a synthetic prostaglandin which shows a greater specificity as regards therapeutic action, thereby eliminating certain disadvantages of $PGE_1$, especially those referred to above.

The compounds of the invention achieve this objective. In actual fact, pharmacological tests carried out with these compounds and for comparison purposes with $PGE_1$ have shown that compounds of formula I, in the same way as $PGE_1$, contact the smooth intestinal and uterine muscles, dilate the blood vessels as well as the bronchi, decrease arterial pressure and inhibit gastric secretion. However the compounds of the invention function in a much more specific manner than $PGE_1$ at the bronchial level and are generally more active as bronchodilatory agents than $PGE_1$.

The compounds of the invention are thus capable of being used therapeutically in the treatment of pathological states which affect the respiratory system, and especially asthma, with substantially none of the secondary effects previously referred to in respect of $PGE_1$.

Derivatives of prostaglandin $E_1$ having a nitrogen atom in the 8-position are already known.

In French Pat. No. 2,304,340 there are described $DL$-8-aza-11-deoxy-$PGE_1$ and esters thereof which are presented as possessing a contracting action on the smooth intestinal and uterine muscles, a vasodilatory effect as well as an inhibiting action on gastric secretion. Furthermore, $DL$-8-aza-11-deoxy-$PGE_1$ and esters thereof, were found to possess a bronchodilatory action which is much more specific than that of $PGE_1$.

However, it was surprisingly discovered that the compounds of the invention are generally more active than $DL$-8-aza-11-deoxy-$PGE_1$.

Furthermore, it has also been found that the bronchodilatory action of the compounds of the invention is still more specific than that of $DL$-8-aza-11-deoxy-$PGE_1$.

Consequently, when used therapeutically in the treatment of pathological states affecting the respiratory system, the compounds of the invention will be likely to present less undesirable side-effects than $DL$-8-aza-11-deoxy-$PGE_1$.

Independently of their pharmacological utility, the 2-pyrrolidinone derivatives of the invention have in addition certain advantages over $PGE_1$, particularly as regards their preparation. $PGE_1$, being a natural product, can be obtained for example by extraction from natural materials, especially from vesicular glands of sheep, lungs of pigs or even from human seminal plasma. It is evident that such sources of supply will only permit this product to be obtained in limited quantities and with the use of expensive equipment, which will have the effect of increasing the cost of the product to a substantial degree.

Furthermore, production of $PGE_1$ by a synthetic route cannot be achieved without considerable difficulty owing to the several centres of asymmetry present in the molecule with the result that the number of stages in the preparation of the compound is multiplied with a consequent increase in the manufacturing cost.

The synthesis of the compounds of formula I in accordance with the invention substantially avoids these difficulties.

Their simpler chemical structure which, in fact, eliminates the asymmetry at the 8 and 11 carbon atom positions of $PGE_1$, has the result of facilitating chemical synthesis. Furthermore, the starting-products required for the preparation of the compounds of the invention can be easily obtained, and hence it will be possible to prepare the compounds of the invention in much larger quantities than is possible when starting from natural tissues as in the case of $PGE_1$.

These important advantages inherent in the preparation of the compounds according to the invention will contribute to their bring shown preference over $PGE_1$.

The results of a number of pharmacological tests carried out with the following compounds of the invention are set out below:

$DL$-8-aza-11-deoxy-16,16-dimethyl-$PGE_1$(Compound 1)

$DL$-8-aza-11-deoxy-15-ethyl-$PGE_1$ (Compound 2)

$DL$-8-aza-11-deoxy-15-0-acetyl-$PGE_1$ (Compound 3)

$DL$-8-aza-11-deoxy-15-methyl-$PGE_1$ ethyl ester (Compound 4)

$DL$-2-methyl-8-aza-11-deoxy-$PGE_1$ (Compound 5)

These pharmacological tests, carried out in comparison with $PGE_1$ and $DL$-8-aza-11-deoxy-$PGE_1$, show the markedly specific nature of the action of the compounds of formula I on the bronchial tubes.

In each of these trials, the compound tested was employed in the form of ethanolic solutions diluted with distilled water.

I. Spasmogenic action on isolated intestine or uterus

For this purpose the MAGNUS technique [Arch. Ges. Physiol. 102, 123 (1904)] was employed.

It was found that, on the ileum of a guinea pig, Compounds 1, 2, 3, 4 and 5 of the invention do not produce any spasm at a dose of $10^{-3}$g/ml of bath, whereas when using $PGE_1$ and $DL$-8-aza-11-deoxy-$PGE_1$ doses of $10^{-6}$g/ml and $5 \times 10^{-3}$g/ml respectively are sufficient to obtain spasms of equal intensity.

This means that the spasmogenic properties of the compounds of the invention are extremely weak and are at least one thousand times weaker than those of $PGE_1$ and at least five times weaker than those of $DL$-8-aza-11-deoxy-$PGE_1$.

Used on the uterus of a rat, which had been blocked prior to the oestral cycle by means of stilboestrol, it was found that $PGE_1$ contracts this organ in an intense and regular manner at a dose of $0.3 \times 10^{-5}$g/ml, whereas it is necessary to introduce into the bath a dose 200 times larger, i.e. $0.6 \times 10^{-3}$g/ml of $DL$-8-aza-11-deoxy-$PGE_1$ in order to obtain an equivalent spasm. As against this, Compounds 1,3, 4 and 5 are totally inactive at a dose of $10^{-3}$g/ml as spasmogenic agents.

II. Cardiovascular action

The effect of different doses of the compounds of the invention, of $PGE_1$ and of $DL$-8-aza-11-deoxy-$PGE_1$ on systolic arterial pressure, diastolic arterial pressure and cardiac frequency was investigated in the conventional manner in dogs.

Administered intraveneously, in a dose of 0.5 to 1μg/kg, $PGE_1$ immediately causes a systemic arterial hypotension having an effect on both the systolic and the diastolic pressure. The mean pressure is reduced, depending on the animal, by between 5% and 21% of its initial value, while a moderate sinusal tachycardia becomes apparent.

As regards, $DL$-8-aza-11-deoxy-$PGE_1$, it was observed that, administered intravenously and in doses between 5 and 50 μg/kg this compound produces the same effects as $PGE_1$ on the cardiovascular system.

With respect to the compounds of the invention, it was observed that at doses below 100 μg/kg of Compound 1, 50 μg/kg of Compound 2, 300 μg/kg of Compound 3 and 200 μg/kg of Compound 5 no inhibitory effect appears on cardiac frequency and arterial pressure.

When administered in the femoral artery of dogs in a dose of 0.01 μg/kg, $PGE_1$ increases the arterial flow by +173%, while 1μg/kg of DL-8-aza-11-deoxy-$PGE_1$ causes a variation of +115% of the initial flow.

With respect to the compounds of the invention, it was observed that no variation of the arterial flow occurred after the administration by the same route of 50 γ/kg of Compound 1, 100 γ/kg of Compound 2, 50 γ/kg of Compound 3 and 100 γ/kg of Compound 5.

At doses of 100 γ/kg of Compound 1, 300 γ/kg of Compound 2, 100 γ/kg of Compound 3 and 100 γ/kg of Compound 5, a slight variation of the arterial flow was registered but it was without any statistical significance. These results show that the compounds of the invention are much less active on the cardiovascular system that $PGE_1$ and DL-8-aza-11-deoxy-$PGE_1$.

III. Bronchodilatory activity on the guinea-pig.

For this purpose the technique developed by KONZETT & ROSSLER (Arch. Exp. Path. Pharmakol., 1940, 195, 71-74) was used, the spasm-promoting agent being acetylcholine.

The results obtained with compounds of the invention in comparison with $PGE_1$ and DL-8-aza-11-deoxy-$PGE_1$ are given in the following Table.

The percentages of reduction of the bronchospasm were calculated at different times after the intravenous administration of 10 μg/kg of the compound under study.

TABLE

| Compound | % of reduction of the bronchospasm after: |
|---|---|
| | 5 minutes |
| Compound 1 | 51 |
| Compound 3 | 51 |
| Compound 4 | 54 |
| DL-8-aza-11-deoxy-$PGE_1$ | 43 |
| $PGE_1$ | 37 |
| | 10 minutes |
| Compound 2 | 28 |
| Compound 3 | 34 |
| Compound 4 | 21 |
| DL-8-aza-11-deoxy-$PGE_1$ | 28 |
| $PGE_1$ | 6 |
| | 15 minutes |
| Compound 2 | 5 |
| Compound 3 | 6 |
| Compound 4 | 6 |
| DL-8-aza-11-deoxy-$PGE_1$ | 0 |
| $PGE_1$ | 0 |

These results show that the compounds are more active than $PGE_1$ and generally more active than DL-8-aza-11-deoxy-$PGE_1$.

Furthermore, judging by the overall pharmacological results, it appears that the bronchodilatory action of the compounds of the invention is more specific than that of $PGE_1$ and DL-8-aza-11-deoxy-$PGE_1$.

It will also be noted that the compounds are still active as bronchodilatory agents after $PGE_1$ and DL-8-aza-11-deoxy-$PGE_1$ have ceased to exert their effect.

The pharmaceutical and veterinary compositions of the invention can be made up in any form which is suitable for their administration in human and veterinary therapy. For ease of administration the composition will normally be made up in a dosage unit form appropriate to the desired mode of administration, for example, a compressed tablet for perlingual administration, a pill, a powder, a capsule, a syrup for oral administration, a suspension for oral or aerosol administration, a suppository for rectal administration, a cream or an ointment for topical or local administration or a sterile solution or suspension for parenteral administration.

The therapeutic compositions of the invention will be prepared in accordance with known techniques by associating at least one compound of the invention with an appropriate diluent or excipient and then if required making up the resulting admixture in the desired dosage unit form. Examples of suitable diluents and excipients are distilled water, ethanol, talc, magnesium stearate, starch and cocoa butter.

The range of active substance used may, for example, be 0.5 μg to 3000 μg daily in 1 to 60 aerosol inhalations for asthma or other affections of the respiratory system.

The following Examples illustrate the preparation of the compounds of the invention.

In these Examples, the analytical results obtained from nuclear magnetic resonance spectra (N.M.R.) comprise the following abbreviations, which indicate:

δ or chemical displacement indicates the dierence between the field forces at which signals are obtained for the nuclei of the same type, such as the proton, but situated in a different molecular environment ppm = part per million $CDCl_3$ = deuterium-containing chloroform, used as reference and as solvent.

In addition, the Rf values indicated in the following Examples were determined by thin layer chromatography using a 20/80 acetone/methylene chloride mixture as solvent.

EXAMPLE 1

Preparation of
DL-ω-carboethoxy-1-hexyl-5-(3'-hydroxy-3'-methyl-1'-octen-(E)-yl)-2-pyrrolidinone or
DL-8-aza-11-deoxy-15-methyl-$PGE_1$ ethyl ester A solution of methyl magnesium iodide was first prepared from 0.213 g (0.0015 mol) of methyl iodide, 10 ml of anhydrous ethyl ether and 0.036 g (about 0.0015 mol) of magnesium turnings. This mixture was cooled to 0° C and then 0.365 g (0.001 mol) was added of DL-ω-carboethoxy-1-hexyl-5-(3'-oxo-1'-octen-(E)-yl)-2-pyrrolidinone dissolved in 10 ml of anhydrous ethyl ether. The reaction medium was stirred at 0° C for 4 hours and then 5 ml of a saturated aqueous solution of ammonium chloride were added. The mixture was stirred at room-temperature for 30 minutes and then extracted by means of 50 ml of ether. The organic phase was dried and concentrated under vacuum.

In this manner, there was obtained 0.500 g of DL-8-aza-11-deoxy-15-methyl-$PGE_1$ ethyl ester in the form of a pale yellow oil. Yield: 78% Rf = 0.62 and 0.66.

I.R. Spectrum ($CHCl_3$): OH at 3440 $cm^{-1}$,
CO (ester) at 1730 $cm^{-1}$,
CO (amide) at 1680 $cm^{-1}$,
CH = CH at 1635 $cm^{-1}$.

N.M.R. Spectrum ($CDCl_3$): δ = 0.9 ppm ($CH_3$),
= 1.25 ppm ($CH_3$ in the 15-position),
= 1.3 ppm ($CH_3$ ester),
= 2.7 ppm (OH),
= 4.1 ppm ($CH_2$ ester),
= 6 to 7 ppm

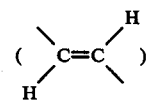

EXAMPLE 2

Preparation of
DL-ω-carboethoxy-1-hexyl-5-(3'-hydroxy-3'-ethyl-1'-octen-(E)-yl)-2-pyrrolidinone or
DL-8-aza-11-deoxy-15-ethyl-PGE₁ ethyl ester A solution of 0.163g (0.0015 mol) of ethyl bromide and 0.036g (0.0015 mol) of magnesium turnings in 10ml of anhydrous ether was cooled to −5° C and treated, at this temperature, for 4 hours by 0.365g of DL-ω-carboethoxy-1-hexyl-5-(3'-oxo-1'-octen-(E)-yl)-2-pyrrolidinone dissolved in 10ml of dry ether. To this reaction medium 5ml of a saturated solution of ammonium chloride was added. The mixture was allowed to stand for 30 minutes and then extracted with ether. The organic phase was washed with 50ml of water and then dried and concentrated.

In this manner, there was obtained the DL-8-aza-11-deoxy-15-ethyl-PGE₁ ethyl ester in a yield of 64% Rf: 0.20 and 0.41.

I.R. Spectrum (CHCl₃): OH at 3440 cm⁻¹,
CO (ester) at 1720 cm⁻¹,
CO (amide) at 1675 cm⁻¹.
N.M.R. Spectrum (CDCl₃): δ = 0.9 ppm (CH₃ in the 15-psoition and CH₃ in the 20-position)
= 4.15 ppm

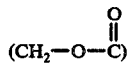

= 5.6 ppm (CH=CH).

Preparation of
DL-ω-carboxy-1-hexyl-5-(3'-hydroxy-3'-ehtyl-1'-octen-(E)-yl)-2-pyrrolidinone or
DL-8-aza-11-deoxy-15-ethyl-PGE₁

A solution of 0.200g (about 0.0005 mol) of DL-ω-carboethoxy-1-hexyl-5-(3'-hydroxy-3'-ethyl-1'-octen-(E)-yl)-2-pyrrolidinone in 15ml of methanol was treated with 10ml of 0.5N-sodium hydroxide at room-temperature for 12 hours. The reaction medium was then extracted with methylene chloride and the aqueous phase was acidified by means of 1N-hydrochloric acid and extracted with methylene chloride. The organic fraction was then dried and concentrated.

In this manner, there was obtained 0.120g of DL-8-aza-11-deoxy-15-ethyl-PGE₁ in the form of a colourless gel. Yield: 56%. Rf = 0.11 and 0.13.

I.R. Spectrum (CHCl₃): OH and COOH at 2500-3500 cm⁻¹,
CO (acid) at 1710 cm⁻¹,
CO (amide) at 1660 cm⁻¹.
N.M.R. Spectrum (CDCl₃): δ = 0.85 ppm (CH₃ in the 15-position and CH₃ in the 20-position)
= 4.45 ppm (OH and COOH)
= 5.6 ppm (CH=CH).

EXAMPLE 4

Preparation of
DL-ω-carboethyoxy-1-hexyl-5-(3'-acetoxy-1'-octen-(E)-yl-2-pyrrolidinone or
DL-8-aza-11-deoxy-15-O-acetyl-PGE₁ ethyl ester To a solution of 0.183g (0.0005 mol) of DL-ω-carboethoxy-1-hexyl-5-(3'-hydroxy-1'-octen-(E)-yl)-2-pyrrolidinone in 10ml of anhydrous methylene chloride was added 1.5ml of dry pyridine. The solution was cooled to 0° C and a solution of 1ml of acetyl chloride in 5ml of anhydrous methylene chloride was added drop-by-drop. The mixture was stirred at room-temperature for 12 hours and then poured into iced water. After extraction with 50ml of methylene chloride, the organic fraction was washed several times with water. The methylene chloride solution was filtered on a silica gel column and the filtrate was concentrated. After washing of the residue with hexane to remove the traces of pyridine, the traces of solvent were eliminated under vacuum.

In this manner, there was obtained 0.180g of DL-8-aza-11-deoxy-15-0-acetyl-PGE₁ ethyl ester in the form of a colourless gel. Yield: 88%. Rf = 0.65.

I.R. Spectrum (CHCl₃): CO(esters) at 1730 cm⁻¹,
CO(amide) at 1670 cm⁻¹,
—O—C— at 1250 cm⁻¹.
N.M.R. Spectrum (CDCl₃)δ: = 0.9 ppm (CH₃),
= 2.05 ppm (—O—COCH₃),
= 4.15 ppm (CH₂—O—CO),
= 5.3 ppm (—CH—O—CO),
= 5.6 ppm (CH=CH).

EXAMPLE 5

Preparation of
DL-ω-carboxy-1-hexyl-5-(3'-acetoxy-1'-octen-(E)-yl)-1-pyrrolidinone or
DL-8-aza-11-deoxy-15-O-acetyl-PGE₁

A mixture of 0.169g (0.0005 mol) of DL-ω-carboxy-1-hexyl-5-(3'-hydroxy-1'-octen-(E)-yl)-2-pyrrolidinone, 10ml of acetic acid and 10ml of distilled water was heated under reflux for 24 hours. The water and the acetic acid were eliminated under vacuum in the presence of benzene. This operation was repeated several times. After that, the residue was washed several times with hexane and the traces of hexane were eliminated under vacuum.

In this manner, there was obtained 0.150g of DL-8-aza-11-deoxy-15-O-acetyl-PGE₁. Yield: 63%. Rf = 0.22.

I.R. Spectrum (film) : CH₃COO at 1250 cm⁻¹,
CO (amide) at 1670 cm⁻¹,
CO (acid) at 1715 cm⁻¹.
N.M.R. Spectrum (CDCl₃)δ: = 2.0 ppm (CH₃CO),
= 5.6 ppm (CH=CH),
= 7.4 ppm (COOH).

EXAMPLE 6

Preparation of
DL-ω-carbomethoxy-1-hexyl-5-(3'-methoxy-1'-octen-(E)-yl)-2-pyrrolidinone or
DL-8-aza-11-deoxy-15-0-methyl-PGE₁ methyl ester To a suspension of 0.050g of sodium hydride previously washed with hexane in 10ml of anhydrous ether, was added 0.169g (about 0.0005 mol) of DL-ω-carboxy-1-hexyl-5-(3'-hydroxy-1'-octen-(E)-yl)-2-pyrrolidinone dissolved in 20ml of anhydrous ether. The reaction medium was stirred for one hour and then 1ml of methyl iodide dissolved in 5ml of anhydrous ether was added at 0° C. The mixture was stirred at room-temperature for 12 hours and 50ml of ether were then added. The ethereal solution was washed with a saturated solution of sodium bicarbonate, dried and the solvent was eliminated.

In this manner, there was obtained 0.040g of DL-8-aza-11-deoxy-15-0-methyl-PGE₁ methyl ester in the form of a pale yellow oil. Rf = 0.66.

I.R. Spectrum (CHCl$_3$): disappearance of OH bands.
CO (ester) at 1730 cm$^{-1}$,
CO (amide) at 1675 cm$^{-1}$.

EXAMPLE 7

Preparation of
DL-ω-carboethoxy-1-hexyl-5-(4',4'-dimethyl-3'-hydroxy-1'-octen (E)-yl)-2-pyrrolidinone or
DL-8-aza-11-deoxy-16,16-dimethyl-PGE$_1$ ethyl ester (A) Dimethyl 2-oxo-3,3-dimethyl-n-heptylphosphonate a) 2,2-Dimethyl-hexanoic acid In a 2l-three-necked flask fitted with a dropping-funnel, a condenser equipped with a calcium chloride trap, a thermometer for low temperature and a mechanical stirrer were introduced 650ml of anhydrous tetrahydrofuran and 101g (1 mol) of diisopropylamine previously dried for 48 hours on calcium hydride. The stirring was started and the mixture was cooled to −20° C. For one hour, 400ml (1 mol) of a 16%- solution of butyl lithium in hexane were added drop-by-drop under nitrogen atmosphere. The temperature of the mixture was maintained at −10° C to −12° C and 44g (0.5 mol) of isobutyric acid freshly distilled were introduced over a period of 20 minutes. The temperature of the reaction medium rose gradually to reach 5° C at the end of the operation of addition. The temperature was then progressively increased by heating to 50° C and this temperature was maintained for 2 hours. The mixture was cooled to 0° C and 68.5g (0.5 mol) of butyl bromide redistilled and dried on a 4 Å screen were added over a period of 20 minutes. The reaction medium was stirred for 2 hours while being allowed to return to room-temperature. The mixture was allowed to stand at room-temperature for 12 hours and then concentrated under vacuum. The residue so obtained was taken up in 300ml of distilled water and 100ml of hexane. This mixture was then stirred for 10 minutes and the aqueous fraction was washed once with 100ml of ether and then acidified with an aqueous solution of 50%-hydrochloric acid. The aqueous phase was extracted with ether and the ethereal solution was washed once with 50ml of distilled water, dried, concentrated and distilled under reduced pressure.

In this manner, there were obtained 49.7g of 2,2-dimethylhexanoic acid in the form of a colourless liquid.
Yield : 64%.

I.R. Spectrum (film) : OH at 2500–3500 cm$^{-1}$
CO at 1700 cm$^{-1}$
CH$_3$ at 1375 cm$^{-1}$.
N.M.R. Spectrum (CDCl$_3$): δ = 0.9 ppm (CH$_3$-CH$_2$),
= 1.1 ppm (CH$_3$-C),
= 1 to 1.7 ppm (CH$_2$),
= 11.5 ppm (OH).

(b) Ethyl 2,2-dimethyl-hexanoate

A mixture of 20.16g (0.14 mol) of 2,2-dimethyl-hexanoic acid, 90ml of absolute ethanol, 40ml of dry benzene and 0.5ml of concentrated sulphuric acid was heated under reflux with a Dean-Stark system for 72 hours. The solvents were eliminated under vacuum and the residue was taken up with methylene chloride. This organic phase was washed with a saturated aqueous solution of sodium bicarbonate and then with distilled water to neutrality. The organic fraction was dried and concentrated.

In this manner, there were obtained 17.8g of ethyl 2,2-dimethylhexanoate in the form of a pale yellow liquid which was homogeneous in thin layer chromatography. Yield : 74%.

I.R. Spectrum (film) : CO (ester) at 1730 cm$^{-1}$,
CH$_3$ at 1375 cm$^{-1}$.

(c) Dimethyl 2-oxo-3,3-dimethyl-n-heptylphosphonate

While stirring under nitrogen atmosphere, 100ml of a solution of butyl lithium in anhydrous ether was added drop-by-drop in a solution of 24.8g of dimethyl methylphosphonate in 160ml of anhydrous tetrahydrofuran. The temperature of the reaction medium was maintained between −50° C and −60° C. After 10 minutes, a solution of 13.76g (0.08 mol) of ethyl 2,2-dimethylhexanoate in 60ml of anhydrous tetrahydrofuran was added drop-by-drop care being taken to maintain the temperature between −65° C and −70° C. The mixture was stirred for 4 hours at the same temperature and then at 0° C for 12 hours. After acidification with 10ml of acetic acid and concentration under vacuum, the mixture was extracted with ether. The ethereal solution was washed several times with water, dried on sodium sulphate, and concentrated.

In this manner, there were obtained 22.5g of crude dimethyl 2-oxo-3,3-dimethyl-n-heptylphosphonate in the form of a yellow liquid and 12.2g of pure colourless product, B.P. : 69°–70° C (15 mm.Hg) Yield: 61%.

N.M.R. Spectrum (CDCl$_3$): δ = 0.9 ppm (CH$_3$ butyl),
= 1.15 ppm ((CH$_3$)$_2$-C),
= 1 to 1.6 ppm (CH$_2$),
= 3.15 ppm (CO-CH$_2$-P),
= 3.8 ppm (OCH$_3$).

(B)
DL-ω-carboethoxy-1-hexyl-5-(4',4'-dimethyl-3'-oxo-1'-octen-(E)-yl)-2-pyrrolidinone Under nitrogen atmosphere and at room-temperature, a solution of 5g (0.02 mol) of dimethyl 2-oxo-3,3-dimethyl-n-heptylphosphonate in 10ml of anhydrous tetrahydrofuran was added drop-by-drop to a suspension of 0.192g of sodium hydride in 60ml of anhydrous tetrahydrofuran. When the solution was limpid, a solution of 5.38g (0.02 mol) of DL-ω-carboethoxy-1-hexyl-5-carboxaldehyde-2-pyrrolidinone in 40ml of anhydrous tetrahydrofuran was added drop-by-drop. Stirring was maintained for 4 hours at 30° C. The reaction medium was acidified with acetic acid and then concentrated under reduced pressure. This residue was taken up in methylene chloride and the organic phase was washed with 100ml of water and dried. The solvent was evaporated off and the ethylenic ketone was purified by chromatography on silica gel plates (merck, F.254) using a 20/80 mixture of acetone/methylene chloride as eluent (Rf = 0.77).

In this manner, there was obtained 3.9g of DL-ω-carboethoxy-1-hexyl-5-(4',4'-dimethyl-3'-oxo-1'-octen-(E)-yl)-2-pyrrolidinone in the form of a yellow oil which was homogeneous in thin layer chromatography. Yield : 54%.

I.R. Spectrum : CO (ester) at 1735 cm$^{-1}$)
CO (amide and in the 15-position) at 1695 cm$^{-1}$
C=C at 1630 cm$^{-1}$.
N.M.R. Spectrum (CDCl$_3$) : δ = 0.9 ppm (CH$_3$ butyl),
= 1.0 ppm ((CH$_3$)$_2$-C—),
= 4.0 ppm (—COOCH$_2$),
= 6.5 ppm (CH=CH).

(C) DL-8-aza-11-deoxy-16,16-dimethyl-PGE$_1$ ethyl ester

To a solution of 0.293g (0.001 mol) of DL-ω-carboethoxy-1-hexyl-5-(4',4'-dimethyl-3'-oxo-1'-octen-(E)-yl)-2-pyrrolidinone in 10ml of anhydrous dimethoxyethane, previously cooled to 0° C, were added under nitrogen atmosphere and by small fractions, 0.070g of sodium borohydride. Stirring was maintained for 4 hours at a temperature between 3° C and 5° C and 10ml of distilled water were added followed by 20ml of a 2%-solution of tartaric acid. The solution was extracted with methylene chloride and the traces of dimethoxyethane were eliminated by several washings with water. The methylene chloride solution was dried and concentrated.

In this manner, there was obtained 0.200g of DL-8-aza-11-deoxy-16,16-dimethyl-PGE$_1$ ethyl ester in the form of a pale yellow liquid which was homogeneous in thin layer chromatography. Yield : 67%. Rf = 0.50.

I.R. Spectrum (film) : OH at 3420 cm$^{-1}$,
CO (ester) at 1735 cm$^{-1}$),
CO (amide + C=C) at 1670 cm$^{-1}$.
N.M.R. Spectrum (CDCl$_3$): δ = 0.9 ppm (CH$_3$ butyl),
= 4.1 ppm (CH$_2$—OCO),
= 5.6 ppm (CH=CH).

EXAMPLE 8

Preparation of
DL-ω-carboxy-1-hexyl-5-(4',4'-dimethyl-3'-hydroxy-1'-octen-(E)-yl)-2-pyrrolidinone or
DL-8-aza-11-deoxy-16,16-dimethyl-PGE$_1$ To a solution of 0.147g of DL-ω-carboethoxy-1-hexyl-5-(4',4'-dimethyl-3'-hydroxy-1'-octen-(E)-yl)-2-pyrrolidinone in 10ml of methanol were added drop-by-drop at 0° C, 5ml of 0.5N-sodium hydroxide. The reaction medium was stirred at room-temperature for 12 hours and then 20ml of water were added. The mixture was extracted with methylene chloride and the aqueous phase was first acidified with 5ml of HCl N and then extracted with methylene chloride. This latter solution was washed with water saturated with sodium chloride, dried and the solvent was eliminated under vacuum.

In this manner, there was obtained 0.100 g of DL-8-aza-11-deoxy-16,16-dimethyl-PGE$_1$ in the form of a colourless gel which was homogeneous in thin layer chromatography.

Yield: 75%.
Rf = 0.20.
I.R. Spectrum (film) : OH at 3340 cm$^{-1}$,
COOH at 2000–3500 cm$^{-1}$,
COOH at 1710 cm$^{-1}$, CO and C=C at 1660 cm$^{-1}$.
N.M.R. Spectrum (CDCl$_3$) : δ = 0.9 ppm (CH$_3$ butyl), = 5.7 ppm (CH=CH), = 6.95 ppm (OH and COOH).

EXAMPLE 9

Preparation of
DL-1-(6'-carboethoxy-6'-methyl-hexyl)-5-(3'-hydroxy-1'-octen(E)-yl)-2-pyrrolidinone or
DL-2-methyl-8-aza-11-deoxy-PGE$_1$ ethyl ester (A)
DL-1-(6'-carboethoxy-6'-methyl-hexyl)-5-(2'-tetrahydropyranyl-oxymethyl)-2-pyrrolidinone A mixture of 10 g (0.05 mol) of 5-(2'-tetrahydropyranyl-oxymethyl)-2-pyrrolidinone, 2 g (about 0.05 mol) of sodium amide and 200 ml of anhydrous toluene was refluxed for one hour. To this solution, 13 g of ethyl 7-bromo-2-methyl-heptanoate in 25 ml of anhydrous toluene were added and the resulting mixture was heated under reflux for 24 hours.

The reaction medium was allowed to return to room-temperature and then poured into 100 ml of iced water. The mixture was decanted and the organic phase was washed once with water saturated with sodium chloride. The aqueous phase was extracted with 50 ml of methylene chloride and this last solution was washed once with water saturated with sodium chloride. The toluene and methylene chloride solutions were collected, dried and concentrated.

In this manner, there were obtained 15 g of DL-1-(6'-carboethoxy-6'-methyl-hexyl)-5-(2'-tetrahydropyranyl-oxymethyl)-2-pyrrolidinone in the form of an oil. Yield: 81%. Rf = 0.50.

N.M.R. Spectrum (CDCl$_3$) : δ = 1.1 ppm (CH$_3$-CH),
= 1.3 ppm (CH$_3$—CH$_2$O),
= 4.15 ppm (—CH$_2$O—),
= 4.6 ppm (O—CH—O).

Following the same procedure as that described above but using the appropriate starting-products, the compounds hereunder were prepared:

Compound

DL-1-(6'-carboethoxy-2'-methyl-hexyl)-5-(2'-tetrahydropyranyloxymethyl)-2-pyrrolidinone Rf = 0.58.
I.R. Spectrum (CHCl$_3$) : CO (ester) at 1720 cm$^{-1}$,
CO (amide) at 1665 cm$^{-1}$.
N.M.R. Spectrum (CDCl$_3$) : δ = 0.9 ppm (CH$_3$), = 1.25 ppm (CH$_3$—CH$_2$—), = 1.3 to 2.1 ppm (CH$_2$—CH, 19P), = 3 to 4 ppm (CH$_2$—OCH, 17P), = 4.15 ppm (CH$_2$O), = 4.65 ppm (CH—O).

DL-1-(6'-carboethoxy-3'-methyl-hexyl)-5-(2'-tetrahydropyranyloxymethyl)-2-pyrrolidinone Rf = 0.5.
N.M.R. Spectrum (CDCl$_3$) : δ = 0.9 ppm (CH$_3$), = 1.25 ppm (CH$_3$—CH$_2$—) = 4.15 ppm (CH$_2$O—CO), = 4.6 ppm (CH—O).

(B)
DL-1-(6'-carboethoxy-6'-methyl-hexyl)-5-hydroxymethyl-2-pyrrolidinone

A solution of 12.3 g (0.033 mol) of DL-1-(6'-carboethoxy-6'-methylhexyl)-5-(2'-tetrahydropyranyl-oxymethyl)-2-pyrrolidinone, 50 ml of ethanol and 50 ml of HCl 1N was stirred at room-temperature for 12 hours. The reaction medium was concentrated under vacuum to half its volume and then extracted with methylene chloride. The solution so obtained was washed with distilled water, dried and concentrated.

In this manner, there were obtained 7.5 g of DL-1-(6'-carboethoxy-6'-methyl-hexyl)-5-hydroxymethyl-2-pyrrolidinone in the form of a pale yellow oil.

Yield: 79%.
Rf = 0.25.
I.R. Spectrum (film) : OH at 3400 cm$^{-1}$, CO (ester) at 1730cm$^{-1}$, CO (amide) at 1670 cm$^{-1}$.
N.M.R. Spectrum (CDCl$_3$) : δ = 1.1 ppm (CH$_3$—CH$_2$), = 1.2 ppm (CH$_3$—CH—) = 2.25 ppm (OH), = 4.1 ppm (—CH$_2$—O—CO).

Following the same procedure as that described above but using the appropriate starting-products, the compounds hereunder were prepared:

Compound

DL-1-(6'-carboethoxy-2'-methyl-hexyl)-5-hydroxymethyl-2-pyrrolidinone

Rf = 0.25.

I.R. Spectrum (film) : OH at 3400 cm$^{-1}$, CO (ester) at 1730 cm$^{-1}$, CO (amide) at 1670 cm$^{-1}$.

N.M.R. Spectrum (CDCl$_3$) : δ = 0.9 ppm (CH$_3$), = 1.25 ppm (CH$_3$—CH—), = 2.25 ppm (OH), = 4.15 ppm (—CH$_2$—O—CO).

DL-1-(6'-carboethoxy-3'-methyl-hexyl)-5-hydroxymethyl-2-pyrrolidinone

Rf = 0.24.
Yield: 70%.
I.R. Spectrum (film): OH at 3400 cm$^{-1}$.
N.M.R. spectrum (CDCl$_3$) : δ = 0.9 ppm (CH$_3$), = 1.25 ppm (CH$_3$—CH$_2$—), = 2.25 ppm (OH), = 4.15 ppm (—CH$_2$—O—CO).

(C) DL-1-(6'-carboethoxy-6'-methyl-hexyl)-5-carboxaldehyde-2-pyrrolidinone

To a mixture of 5.7 g (0.02 mol) of DL-1-(6'-carboethoxy-6'-methylhexyl)-5-hydroxymethyl-2-pyrrolidinone, 12.4 g of dicyclohexylcarbodiimide, 60 ml of anhydrous dimethylsulphoxide and 120 ml of anhydrous benzene stirred under nitrogen atmosphere and cooled to 0° C was added drop-by-drop 1.06 ml of dichloroacetic acid. The reaction medium was stirred at roomtemperature for 12 hours. After that, 4.4 g of oxalic acid were added by small fractions and 0° C. Stirring was maintained for 30 minutes and the mixture was then filtered. The precipitate was washed with benzene and the filtrate was diluted to 300 ml with chloroform. The solution was washed with a saturated solution of sodium bicarbonate and then several times with distilled water. After drying, the solvents were eliminated under vacuum and the residue was taken up in 50 ml of ether. The solution so obtained was allowed to stand for 10 minutes, filtered and the filtrate was concentrated under vacuum. These latter operations were effected three times with a view to eliminating the precipitate which is only slightly soluble in ether.

In this manner, there were obtained 5 g of DL-1-(6'-carboethoxy-6'-methyl-hexyl)-5-carboxaldehyde-2-pyrrolidinone.

Rf = 0.34.

I.R. Spectrum (film) : OH (weak enol) at 3300 cm$^{-1}$, CO (ester) at 1735 cm$^{-1}$, CO (amide and aldehyde) at 1690 cm$^{-1}$.

N.M.R. Spectrum (CDCl$_3$) : δ = 1.1 ppm (CH$_3$—CH—), = 1.2 ppm (CH$_3$—CH$_2$), = 4.15 ppm (CH$_2$O—CO), = 9.6 ppm (CHO).

Following the same procedure as that described above but using the appropriate starting-products, the compounds hereunder were prepared.

Compound

DL-1-(6'-carboethoxy-2'-methyl-hexyl)-5-carboxaldehyde-2-pyrrolidinone

Rf = 0.35.

N.M.R. Spectrum (CDCl$_3$) : δ = 0.9 ppm (CH$_3$), = 1.25 ppm (CH$_3$—CH$_2$—), = 4.15 ppm (CH$_2$O—CO), = 9.6 ppm (CHO).

DL-1-(6'-carboethoxy-3'-methyl-hexyl)-5-carboxaldehyde-2-pyrrolidinone

Rf = 0.35.

Yield: 70%.

I.R. Spectrum (CHCl$_3$): OH (weak enol) at 3300 cm$^{-1}$, CO (ester) at 1730 cm$^{-1}$, CO (amide and aldehyde) at 1670 cm$^{-1}$.

N.M.R. Spectrum (CDCl$_3$) : δ = 0.9 ppm (CH$_3$), = 1.25 ppm (CH$_3$—CH$_2$—), = 4.15 ppm (CH$_2$O—CO), = 9.6 ppm (CHO).

(D) DL-1-(6'-carboethoxy-6'-methyl-hexyl)-5-(3'-oxo-1'-octen(E)-yl)-2-pyrrolidinone A mixture of 2.83 g (0.01 mol) of DL-1-(6'carboethoxy-6'-methylhexyl)-5-carboxaldehyde-2-pyrrolidinone, 3.54 g of triphenylphosphoranylidene-2-heptanone, 60 ml of anhydrous dioxane and 120 ml of anhydrous benzene was refluxed for 12 hours. The reaction medium was concentrated under vacuum and the residual oil was taken up in 20 ml of ether. The solution was filtered, the solvent was elminated and the residue was purified by chromatography on silica gel plates.

In this manner, there was obtained DL-1-(6'-carboethoxy-6'-methylhexyl)-5-(3'-oxo-1'-octen-(E)-yl)-2-pyrrolidinone in the form of a pale yellow oil.

Yield: 63%.
Rf = 0.75.

N.M.R. Spectrum (CDCl$_3$) : δ = 0.9 ppm (CH$_3$), = 1.1 ppm (CH$_3$—CH—), = 1.2 ppm (CH$_3$CH$_2$—O) = 4.1 ppm (CH$_2$—O—), about 5.9 to 6.7 ppm (CH=CH).

Following the same procedure as that described above but using the appropriate starting-products, the compounds hereunder were prepared:

Compound

DL-1-(6'-carboethoxy-2'-methyl-hexyl)-5-(3'-oxo-1'-octen-(E)-yl)-2-pyrrolidinone Rf = 0.78.

N.M.R. Spectrum (CDCl$_3$) : δ = 0.9 ppm (CH$_3$, 6P), = 1.75 ppm (CH$_3$ ester), = 4.15 ppm (—CH$_2$—O), = 5.8 to 6.5 ppm (CH=CH).

DL-1-(6'-carboethoxy-3'-methyl-hexyl)-5-(3'-oxo-1'-octen-(E)-yl)-2-pyrrolidinone Rf = 0.77.

N.M.R. Spectrum (CDCl$_3$) : δ = 0.9 ppm (CH$_3$, 6P), = 1.25 ppm (CH$_3$—CH$_2$), =4.15 ppm (CH$_2$—O), = 6 to 6.5 ppm (CH=CH).

(E) DL-2-methyl-8-aza-11-deoxy-PGE$_1$ ethyl ester

A solution of 0.379 g (0.001 mol) of DL-1-(6'-carboethoxy-6'-methyl hexyl-5-(3'-oxo-1'-octen-(E)-yl)-2-pyrrolidinone in 10 ml of anhydrous dimethoxyethane was cooled to 0° C. To this solution, 0.090 g of sodium borohydride was added by small fractions. The mixture was allowed to react at 3° C for 3 hours and then 5 ml of water followed by 5 ml of a 2%-aqueous solution of tartaric acid were added with precautions. After extraction with methylene chloride, the solution so obtained was washed with water saturated with sodium chloride, dried and concentrated under vacuum. The residue so obtained was chromatographed on a silica gel column and a first elution was carried out with ether in order to eliminate the impurities, followed by a second elution with a 20/80 acetone/methylene chloride mixture.

In this manner, there was obtained 0.250 g of DL-2-methyl-8-aza-11-deoxy-PGE$_1$ ethyl ester in the form of a pale yellow oil which was homogeneous in thin layer chromatography. Yield: 65%. Rf = 0.40.

I.R. Spectrum (CHCl$_3$):OH at 3520 cm$^{-1}$,
CO (ester) at 1720 cm$^{-1}$,
CO (amide) at 1665 cm$^{-1}$.
N.M.R. Spectrum (CDCl$_3$):δ = 0.9 ppm (CH$_3$),
about 1.1 ppm (CH$_3$—CH) and (CH$_3$—CH$_2$O),
= 4.15 ppm (CH$_2$—O),
= 5.65 ppm (CH=CH).

Following the same procedure as that described above but using the appropriate starting-products, the compounds hereunder were prepared:

Compound

DL-6-methyl-8-aza-11-deoxy-PGE$_1$ ethyl ester

Rf = 0.42.
I.R. Spectrum (CHCl$_3$):OH at 3525 cm$^{-1}$,
CO (ester) at 1720 cm$^{-1}$,
CO (amide) at 1668 cm$^{-1}$.
N.M.R. Spectrum (CDCl$_3$):δ = 0.9 ppm (CH$_3$, 6P),
= 1.25 ppm (CH$_3$ ester),
= 4.15 ppm (CH$_2$—O),
= 5.65 ppm (CH=CH).

DL-5-methyl-8-aza-11-deoxy-PGE$_1$ ethyl ester

Rf = 0.40.
Yield: 78%.
I.R. Spectrum (CHCl$_3$):OH at 3520 cm$^{-1}$,
CO (ester) at 1720 cm$^{-1}$,
CO (amide) at 1665 cm$^{-1}$.
N.M.R. Spectrum (CDCl$_3$):δ = 0.9 ppm (CH$_3$, 6P),
= 1.2 ppm (CH$_3$—CH$_2$),
= 4.15 ppm (CH$_2$—O),
= 5.67 ppm (CH=CH).

EXAMPLE 10

Preparation of DL-1-(6'-carboxy-6'-methyl-hexyl)-5-(3'-hydroxy-1'-octen-(E)-yl)-2-pyrrolidinone or DL-2-methyl-8-aza-11-deoxy-PGE$_1$ A solution of 0.190 g (0.0005 mol) of DL-1-(6'-carboethoxy-6'-methylhexyl)-5-(3'-hydroxy-1'-octen-(E)-yl)-2-pyrrolidinone in 10 ml of methanol and 10 ml of sodium hydroxide 0.5N was stirred under nitrogen atmosphere at room-temperature for 12 hours. The reaction medium was concentrated to half its volume and 20 ml of water were added. The mixture was extracted with ether and the aqueous phase was acidified with 10 ml of hydrochloric acid 1N and then extracted with methylene chloride. The solution so obtained was washed with water and saturated with sodium chloride. After drying, the solvent was evaporated off under vacuum.

In this manner, there was obtained 0.150 g of DL-2-methyl-8-aza-11-deoxy-PGE$_1$ in the form of a colourless gel which was homogeneous in thin layer chromatography. Yield:85%. Rf:0.13.

I.R. Spectrum (CHCl$_3$):OH large at 2200 to 3500 cm$^{-1}$,
CO (acid) at 1700cm$^{-1}$,
CO (amide) at 1660 cm$^{-1}$.
N.M.R. Spectrum (CDCl$_3$):δ = 0.9 ppm (CH$_3$),
= 5.65 ppm (CH=CH),
= 7.05 ppm (OH and COOH).

Following the same procedure as that described above but using the appropriate starting-products, the compounds hereunder were prepared:

Compound

DL-6-methyl-8-aza-11-deoxy-PGE$_1$

Rf = 0.15.
I.R. Spectrum (CHCl$_3$):OH (large) at 2200–3500 cm$^{-1}$,
CO (acid) at 1700 cm$^{-1}$,
CO (amide) at 1660 cm$^{-1}$.
N.M.R. Spectrum (CDCl$_3$):δ = 0.9 ppm (CH$_3$, 6P),
= 5.64 ppm (CH=CH),
= 7.05 ppm (OH and COOH),
disappearance of the protons CH$_3$CH$_2$— of the ester.

DL-5-methyl-8-aza-11-deoxy-PGE$_1$

Rf = 0.14.
Yield: about 36%.
I.R. Spectrum (CHCl$_3$): OH (large) at 2210–3500 cm$^{-1}$,
CO (acid) at 1700 cm$^{-1}$,
CO (amide) at 1660 cm$^{-1}$.
N.M.R. Spectrum (CDCl$_3$):δ = 0.9 ppm (CH$_3$, 6P),
= 5.6 ppm (CH=CH),
= 6 ppm (OH and COOH, 2P).

EXAMPLE 11

For the particular purpose of treating affections of the respiratory tract, an aerosol was prepared in accordance with known techniques comprising as active ingredient 2 mg of DL-8-aza-11-deoxy-16,16-dimethyl-PGE$_1$ together with an inert propellant and 10 g of ethanol.

We claim:

1. DL-ω-carboethoxy-1-hexyl-5-(3'-hydroxy-3'-methyl-1'-octen-(E)-yl)-2-pyrrolidinone of the formula:

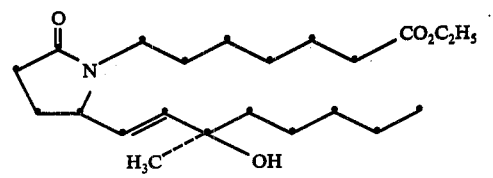

in the form of a racemic mixture or the D isomer or L isomer.

2. DL-ω-carboethoxy-1-hexyl-5-(3'-hydroxy-3'-ethyl-1'-octen-(E)-yl)-2-pyrrolidinone of the formula:

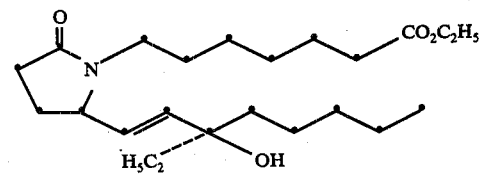

in the form of a racemic mixture or the D isomer or L isomer.

3. DL-ω-carboxy-1-hexyl-5-(3'-hydroxy-3'-ethyl-1'-octen-(E)-yl)-2-pyrrolidinone of the formula:

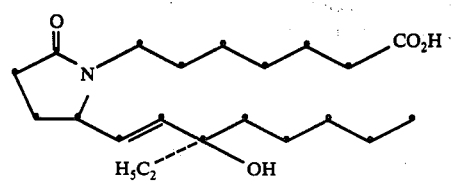

in the form of a racemic mixture or the D isomer or L isomer.

4. DL-ω-carboethoxy-1-hexyl-5-(3'-acetoxy-1'-octen-(E)-yl)-2-pyrrolidinone of the formula:

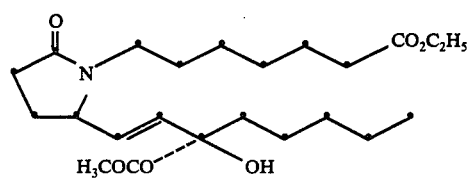

in the form of a racemic mixture or the D isomer or L isomer.

5. DL-ω-carboxy-1-hexyl-5-(3'-acetoxy-1'-octen-(E)-yl)-2-pyrrolidinone of the formula:

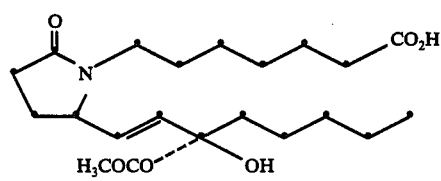

in the form of a racemic mixture or the D isomer or L isomer.

6. DL-ω-carbomethoxy-1-hexyl-5-(3'-methoxy-1'-octen-(E)-yl)-2-pyrrolidinone of the formula:

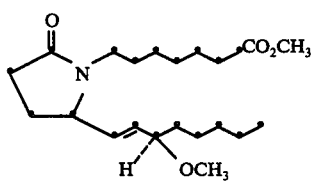

in the form of a racemic mixture or the D isomer or L isomer.

7. DL-ω-carboethoxy-1-hexyl-5-(4',4'-dimethyl-3'-hydroxy-1'-octen-(E)-yl)-2-pyrrolidinone of the formula:

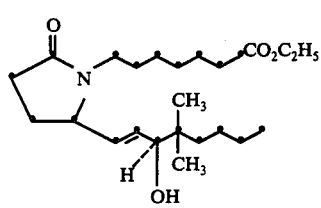

in the form of a racemic mixture or the D isomer or L isomer.

8. DL-ω-carboxy-1-hexyl-5-(4',4'-dimethyl-3'-hydroxy-1'-octen-(E)-yl)-2-pyrrolidinone of the formula:

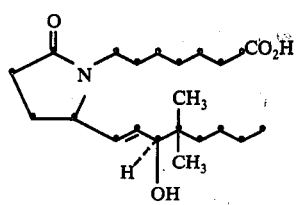

in the form of a racemic mixture or the D isomer or L isomer.

9. DL-1-(6'-carboethoxy-6'-methyl-hexyl)-5-(3'-hydroxy-1'-octen-(E)-yl)-2-pyrrolidinone of the formula:

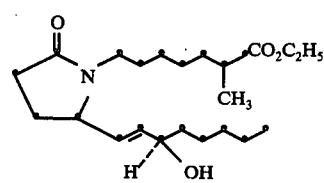

in the form of a racemic mixture or the D isomer or L isomer.

10. DL-1-(6'-carboxy-6'-methyl-hexyl)-5-(3'-hydroxy-1'-octen-(E)-yl)-2-pyrrolidinone of the formula:

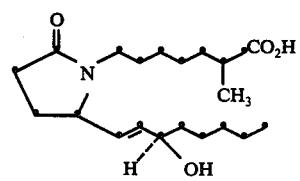

in the form of a racemic mixture or the D isomer or L isomer.

11. DL-1-(6'-carboethoxy-2'-methyl-hexyl)-5-(3'-hydroxy-1'-octen-(E)-yl)-2-pyrrolidinone of the formula:

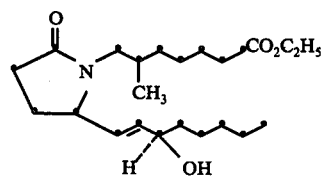

in the form of a racemic mixture or the D isomer or L isomer.

12. DL-1-(6'-carboxy-2'-methyl-hexyl)-5-(3'-hydroxy-1'-octen-(E)-yl)-2-pyrrolidinone of the formula:

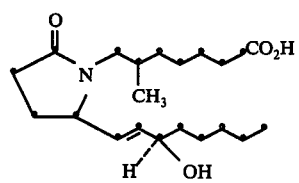

in the form of a racemic mixture or the D isomer or L isomer.

13. DL-1-(6'-carboethoxy-3'-methyl-hexyl)-5-(3'-hydroxy-1'-octen-(E)-hexyl)-5-(3'-hydroxy-1'-octen-(E)-yl)-2-pyrrolidinone of the formula:
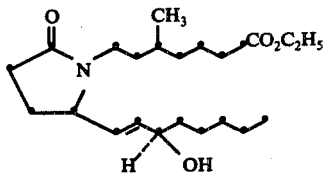
in the form of a racemic mixture or the D isomer or L isomer.
14. DL-1-(6'-carboxy-3'-methyl-hexyl)-5-(3'-hydroxy-1'-octen-(E)-yl)-2-pyrrolidinone of the formula:
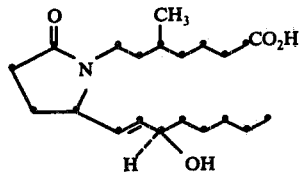
in the form of a racemic mixture or the D isomer or L isomer.
* * * * *